US012623514B2

(12) United States Patent
Bertolini et al.

(10) Patent No.: US 12,623,514 B2
(45) Date of Patent: May 12, 2026

(54) VEHICLE SCENT DIFFUSING SYSTEM

(71) Applicant: Ford Global Technologies, LLC, Dearborn, MI (US)

(72) Inventors: Caio Vinicius Bertolini, Lauro de Freitas (BR); Fabio Cuzziol, São Bernardo do Campo (BR); Danilo Machado Martins, Salvador (BR); Leandro Quinelato, Salvador (BR)

(73) Assignee: Ford Global Technologies, LLC, Dearborn, MI (US)

( * ) Notice: Subject to any disclaimer, the term of this patent is extended or adjusted under 35 U.S.C. 154(b) by 755 days.

(21) Appl. No.: 18/075,580

(22) Filed: Dec. 6, 2022

(65) Prior Publication Data

US 2024/0181848 A1    Jun. 6, 2024

(51) Int. Cl.
B60H 3/00         (2006.01)
A61L 9/12         (2006.01)

(52) U.S. Cl.
CPC .............. B60H 3/0021 (2013.01); A61L 9/12 (2013.01); B60H 3/0035 (2013.01); A61L 2209/11 (2013.01); A61L 2209/15 (2013.01); A61L 2209/16 (2013.01); B60H 2003/0042 (2013.01)

(58) Field of Classification Search
None
See application file for complete search history.

(56) References Cited

U.S. PATENT DOCUMENTS

| | | | |
|---|---|---|---|
| 5,429,180 A | 7/1995 | Nishino et al. | |
| 10,427,502 B1 * | 10/2019 | Izaguirre .............. | B60H 3/0007 |
| 2006/0005711 A1 | 1/2006 | Olefson | |

| | | | |
|---|---|---|---|
| 2008/0139102 A1 | 6/2008 | Major | |
| 2017/0267070 A1 | 9/2017 | Sawyer | |
| 2017/0368915 A1 | 12/2017 | Starke | |

(Continued)

FOREIGN PATENT DOCUMENTS

| | | | | |
|---|---|---|---|---|
| EP | 2221202 A1 | 8/2010 | | |
| FR | 3092278 A1 * | 8/2020 | ........... | B60H 3/0021 |

(Continued)

OTHER PUBLICATIONS

Feuillade et al. FR3092278A1-translated document (Year: 2020).*
Yuzuru, Y. JP2015039893A-translated document (Year: 2015).*

*Primary Examiner* — Jelitza M Perez

(74) *Attorney, Agent, or Firm* — Vichit Chea; Price Heneveld LLP

(57)         ABSTRACT

A scent diffusing system for a vehicle includes a heating, ventilation, and air conditioning (HVAC) system is in fluid communication with a passenger compartment. A duct assembly extends between the HVAC system and the passenger compartment. The duct assembly includes a duct including a receiving extension defining a receiving cavity. The receiving extension defines locating tracks. A holder assembly is slidably received within the locating tracks. An interior of the holder assembly is in fluid communication with an interior of the duct via openings defined by the holder assembly. A scented pad is disposed within the interior of the holder assembly. A controller is configured to activate the HVAC system to direct air through the duct, through the interior of the holder assembly, and into the passenger compartment to diffuse a scent within the passenger compartment.

20 Claims, 9 Drawing Sheets

(56) References Cited

U.S. PATENT DOCUMENTS

| 2018/0370335 | A1 | | 12/2018 | Sawyer | |
| 2019/0184792 | A1 | | 6/2019 | Watanabe | |
| 2021/0323384 | A1 | * | 10/2021 | Sakai | ................. B60H 1/00985 |

FOREIGN PATENT DOCUMENTS

| JP | H0834227 | A | | 2/1996 | |
| JP | 2004216924 | A | | 8/2004 | |
| JP | 2006044389 | A | | 2/2006 | |
| JP | 2006341666 | A | | 12/2006 | |
| JP | 2010089714 | A | | 4/2010 | |
| JP | 2015039893 | A | * | 3/2015 | .......... B60H 3/0021 |
| KR | 19990031033 | A | | 5/1999 | |
| KR | 20070063088 | A | | 6/2007 | |

* cited by examiner

VEHICLE SCENT DIFFUSING SYSTEM

FIELD OF THE DISCLOSURE

The present disclosure generally relates to a scent diffusing system. More specifically, the present disclosure relates to a scent diffusing system for a vehicle.

BACKGROUND OF THE DISCLOSURE

Many vehicles include passenger cabins. Passengers can bring air fresheners into the passenger cabin to impart an aroma within the passenger cabin.

SUMMARY OF THE DISCLOSURE

According to at least one aspect of the present disclosure, a scent diffusing system for a vehicle includes a passenger compartment. A heating, ventilation, and air conditioning system is in fluid communication with the passenger compartment. A controller is in communication with the heating, ventilation, and air conditioning system. A duct assembly extends between the heating, ventilation, and air conditioning system and the passenger compartment. The duct assembly includes a duct including a receiving extension defining a receiving cavity. The receiving extension defines locating tracks. A holder assembly is slidably received within the locating tracks. An interior of the holder assembly is in fluid communication with an interior of the duct via openings defined by the holder assembly. A scented pad is disposed within the interior of the holder assembly. The controller is configured to activate the heating, ventilation, and air conditioning system to direct air through the duct, through the interior of the holder assembly, and into the passenger compartment to diffuse a scent within the passenger compartment.

According to another aspect of the present disclosure, a vehicle duct assembly for a heating, ventilation, and air conditioning system includes a duct including a receiving extension defining a receiving cavity. The receiving extension defines locating tracks. A holder assembly is selectively disposed within the receiving cavity. The holder assembly includes slides configured to be slidably received within the locating tracks. An interior of the holder assembly is in fluid communication with an interior of the duct via openings defined by the holder assembly. A scented pad is disposed within the interior of the holder assembly. Air directed through the duct by said heating, ventilation, and air conditioning system flows through the interior of the holder assembly to diffuse a scent within the air.

According to another aspect of the present disclosure, a duct assembly for a vehicle includes a duct with a receiving extension defining a receiving cavity. The receiving extension defines apertures in a connecting wall thereof. A holder assembly is configured to receive a scented pad. The holder assembly includes a body that defines an opening. An interior of the body is in fluid communication with an interior of the duct via the openings. Snap features are coupled to the body, wherein the snap features are selectively disposed within the apertures to couple the holder assembly to the receiving extension. A lever is coupled to the snap features. The lever is configured to disengage the snap features from the apertures in response to a predefined force.

These and other aspects, objects, and features of the present disclosure will be understood and appreciated by those skilled in the art upon studying the following specification, claims, and appended drawings.

BRIEF DESCRIPTION OF THE DRAWINGS

The following is a description of the figures in the accompanying drawings. The figures are not necessarily to scale, and certain features and certain views of the figures may be shown exaggerated in scale or in schematic in the interest of clarity and conciseness.

In the drawings.

DETAILED DESCRIPTION

Additional features and advantages of the presently disclosed device will be set forth in the detailed description which follows and will be apparent to those skilled in the art from the description, or recognized by practicing the device as described in the following description, together with the claims and appended drawings.

Figure 1:
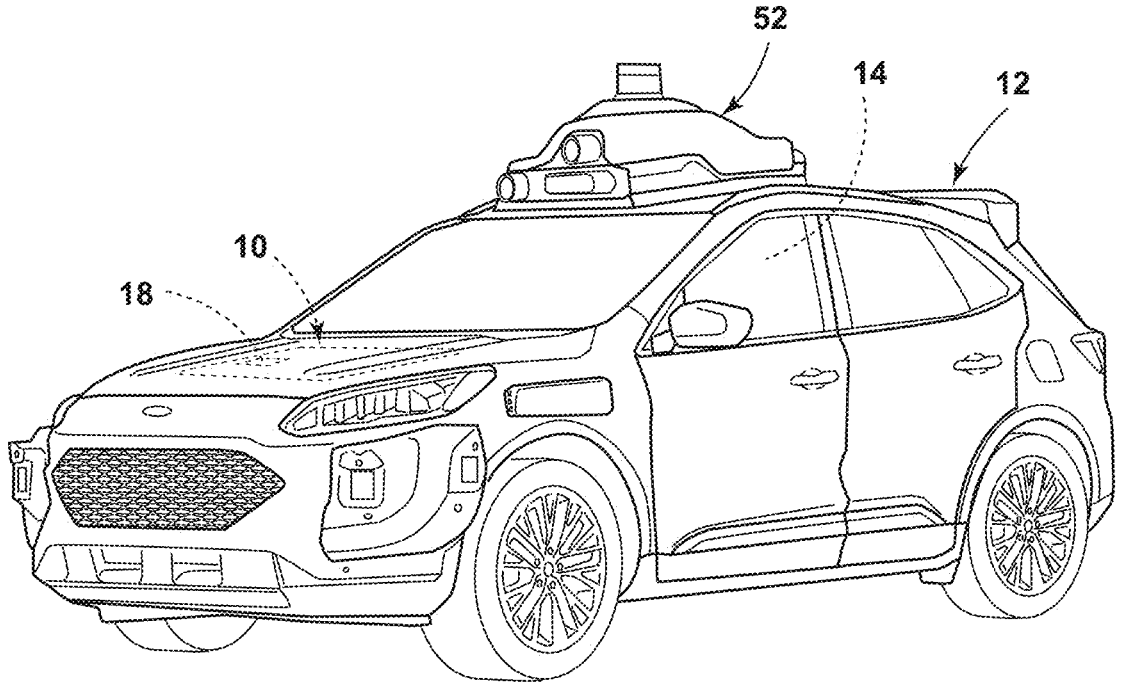
FIG. 1 is a side perspective view of a vehicle having a scent diffusing system, according to the present disclosure.

For purposes of description herein, the terms "upper," "lower," "right," "left," "rear," "front," "vertical," "horizontal," and derivatives thereof shall relate to the concepts as oriented in FIG. 1. However, it is to be understood that the concepts may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

As used herein, the term "and/or," when used in a list of two or more items, means that any one of the listed items can be employed by itself, or any combination of two or more of the listed items, can be employed. For example, if a composition is described as containing components A, B, and/or C, the composition can contain A alone; B alone; C alone; A and B in combination; A and C in combination; B and C in combination; or A, B, and C in combination.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about," and one not modified by "about." It will be further understood that the end-points of each of the ranges are significant both in relation to the other end-point, and independently of the other end-point.

As used herein the terms "the," "a," or "an," mean "at least one," and should not be limited to "only one" unless explicitly indicated to the contrary. Thus, for example, reference to "a component" includes embodiments having two or more such components unless the context clearly indicates otherwise.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

With reference to FIGS. 1-12, reference numeral 10 generally designates a scent diffusing system for a vehicle 12 that includes a passenger compartment 14 and a heating, ventilation, and air conditioning (HVAC) system 16 in fluid communication with the passenger compartment 14. A controller 18 is in communication with the HVAC system 16. A duct assembly 20 extends between the HVAC system 16 and the passenger compartment 14. The duct assembly 20 includes a duct 22 with a receiving extension 24 defining a receiving cavity 26. The receiving extension 24 defines locating tracks 28, 30. The duct assembly 20 also includes a holder assembly 32 slidably received within the locating tracks 28, 30. An interior 34 of the holder assembly 32 is in fluid communication with an interior 36 of the duct 22 via openings 38 defined by the holder assembly 32. The duct assembly 20 also includes a scented pad 40 disposed within the interior 34 of the holder assembly 32. The controller 18 is configured to activate the HVAC system 16 to direct air through the duct 22, through the interior 34 of the holder assembly 32, and into the passenger apartment to diffuse a scent within the passenger compartment 14.

Figure 2:
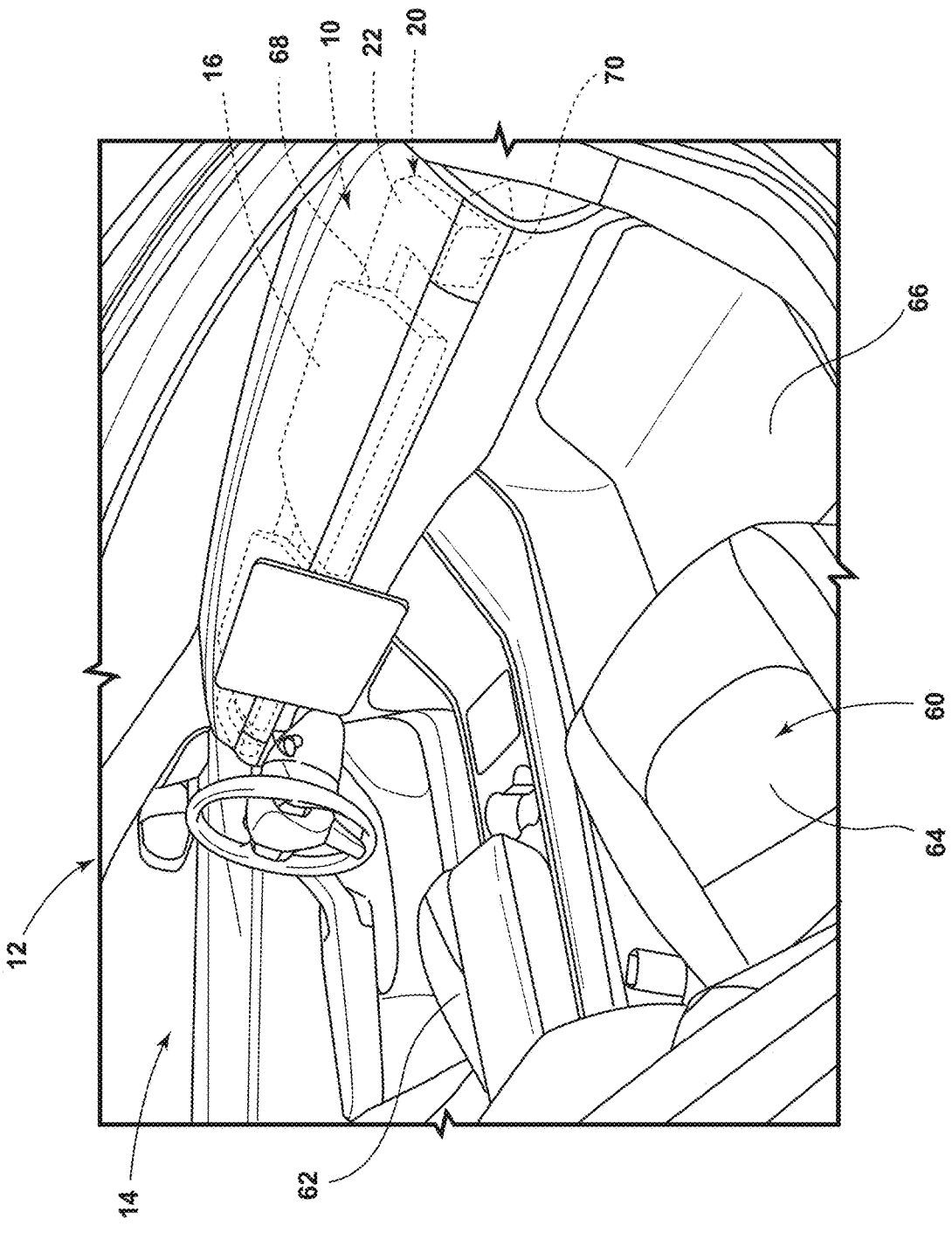
FIG. 2 is a partial side perspective view of a passenger compartment of a vehicle having a scent diffusing system, according to the present disclosure.

Referring to FIGS. 1 and 2, the vehicle 12 is illustrated as an autonomous vehicle 12 having one or multiple sensor assemblies 52 for gathering data to be communicated and processed by the controller 18 or other computing devices. Autonomous vehicles 12 use a variety of sensors 52 and computing devices, including controller 18, to operate the vehicle 12 with various levels of interaction from a human driver. The computing devices of the vehicle 12 may operate the vehicle 12 in an autonomous mode, a semi-autonomous mode, or a non-autonomous mode.

The autonomous mode is one in which each of a propulsion system, a braking system, and a steering system is controlled by the computing devices. In the semi-autonomous mode, the computing devices control one or two of the propulsion, the breaking, and the steering systems of the vehicle 12, and the human operator controls the other system or systems. In the non-autonomous mode, the human operator controls the propulsion, the breaking, and the steering systems of the vehicle 12. It is contemplated that the vehicle 12 may be a fully autonomous vehicle 12 (e.g., operated without the human operator), a partially autonomous vehicle 12 (e.g., operated with or without the human operator), or a manually operated vehicle 12 (e.g., operated with the human operator) without departing the teachings herein. Further, the vehicle 12 may switch between the autonomous, the semi-autonomous, and the non-autonomous modes.

The vehicle 12 may be a sedan, a sport-utility vehicle, a van, a truck, a crossover, other wheeled motor vehicles 12, or other styles of vehicles 12. The vehicle 12 may be used for personal and/or commercial purposes, such as, for ride-providing services (e.g., chauffeuring), transporting, deliveries, ride-sharing services, etc. In certain aspects, the vehicle 12 may be utilized for ride-providing and ride-sharing services where the vehicle 12 is used by multiple passengers each day. The scent diffusing system 10 is configured to operate in conjunction with the die-providing or ride-sharing services to diffuse the scent within the passenger compartment 14 prior to the entry of each new passenger as described further herein.

Referring still to FIGS. 1 and 2, the vehicle 12 includes the passenger compartment 14 with multiple seating assemblies 60 for supporting passengers thereon. As illustrated in FIG. 2, a front seating row includes a driver seat 62 and a passenger seat 64 each disposed in a vehicle-forward portion of the vehicle 12.

The vehicle 12 includes the HVAC system 16 generally disposed in the vehicle-forward portion of the vehicle 12. The HVAC system 16 typically provides conditioned air into the passenger compartment 14. The HVAC system 16 can clean, cool, heat, regulate, ventilate, and/or dehumidify the air that is directed into the passenger compartment 14. The air that is conditioned by the HVAC system 16 is directed to the passenger compartment 14 via ducting, such as the duct 22 included in the scent diffusing system 10.

The duct 22 extends between the HVAC system 16 and a foot space 66 for the front passenger seat 64. The duct 22 may extend to additional or alternative locations within the vehicle 12 without departing from the teachings herein. Further, it is contemplated that the scent diffusing system 10 may include the duct assembly 20 with a single duct 22 or multiple ducts 22 for diffusing the scent. The duct 22 has an inlet 68 in fluid communication with the HVAC system 16 to receive the conditioned air, and an outlet 70 proximate to the foot space 66 of the passenger seat 64 (e.g., a passenger seating area within the passenger compartment 14), generally under a glove box area.

Figure 3:
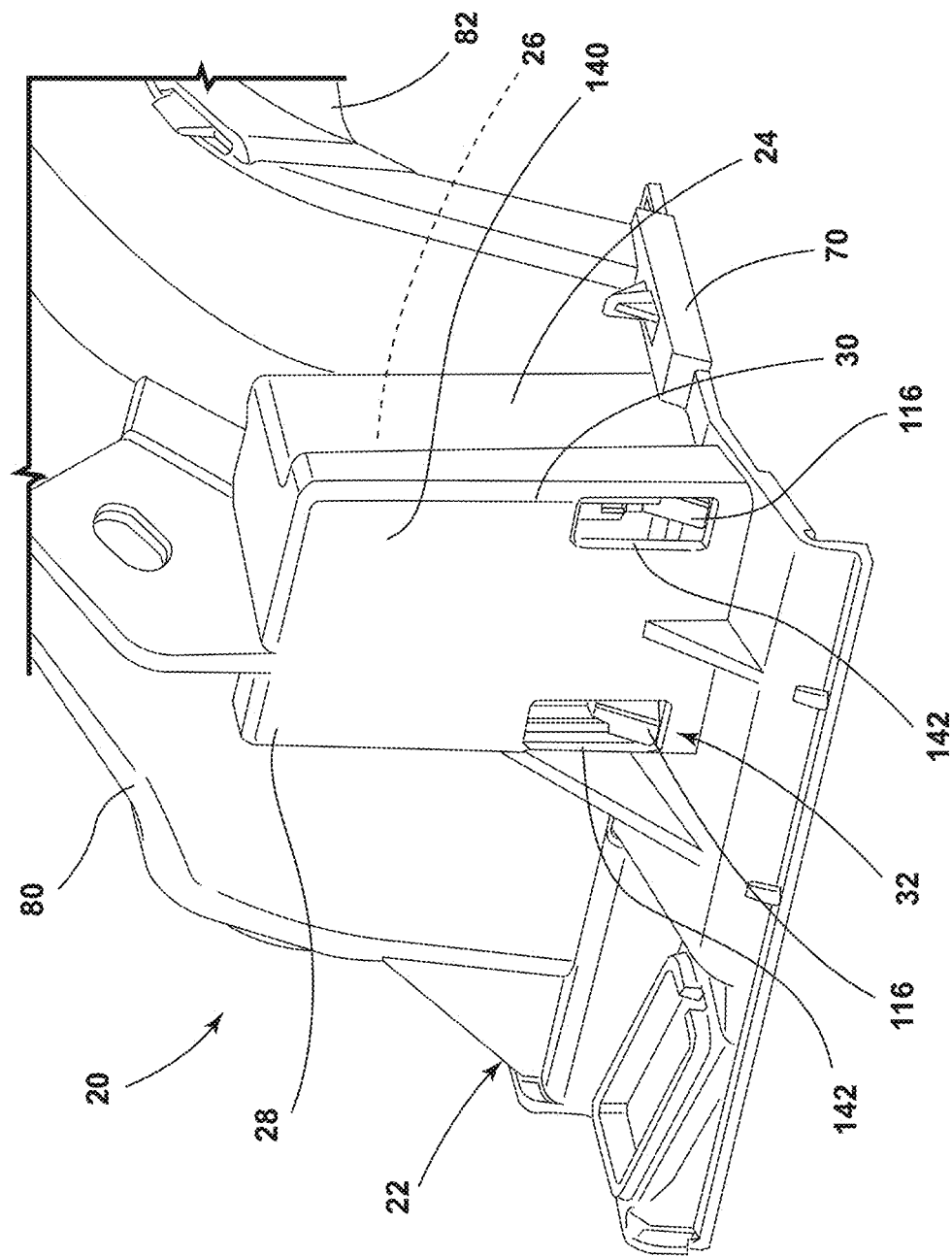
FIG. 3 is a partial side perspective view of a duct assembly for a scent diffusing system, according to the present disclosure.
Figure 4:
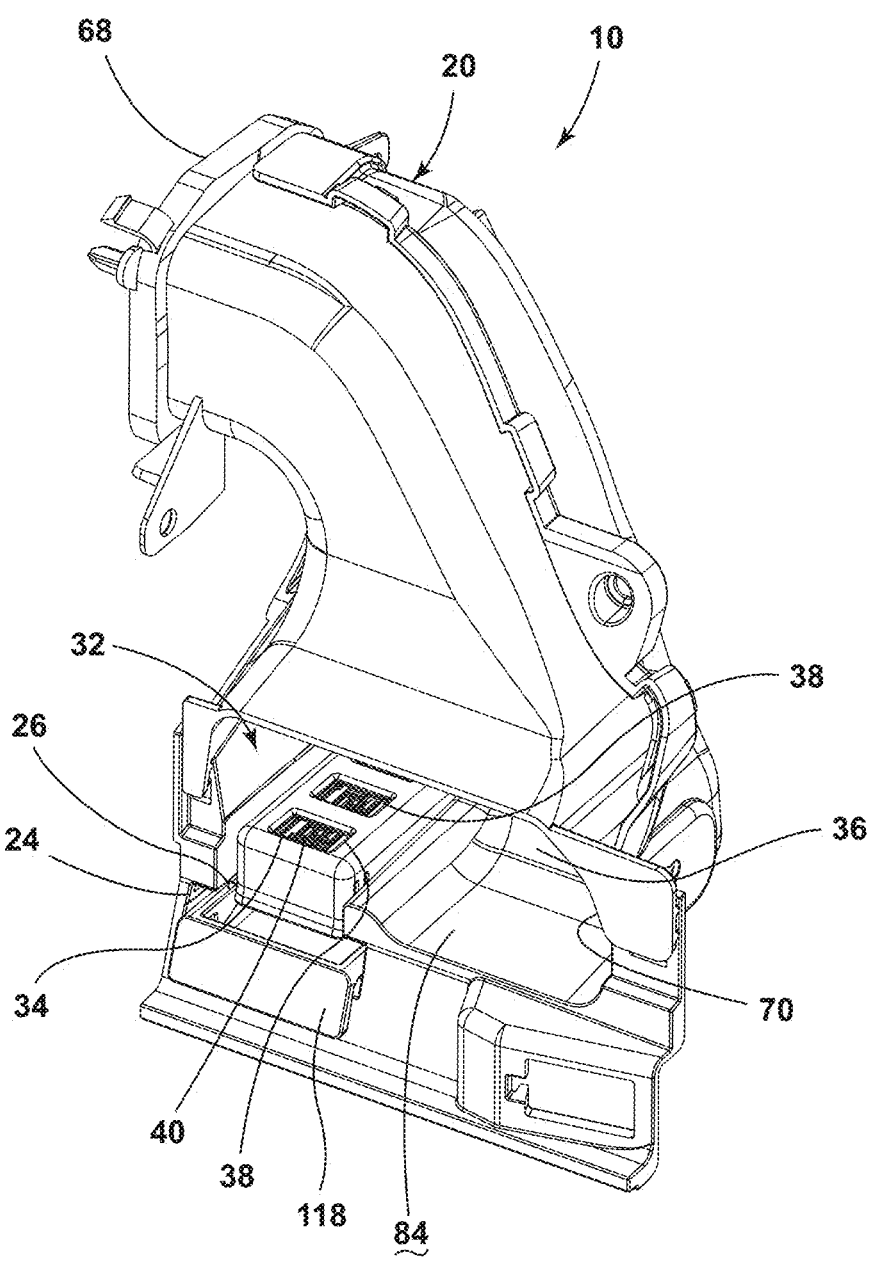
FIG. 4 is a side perspective view of a duct assembly with a holder assembly within a receiving cavity, according to the present disclosure.

Referring to FIGS. 3 and 4, the duct assembly 20 that is utilized for diffusing the scent within the passenger compartment 14. The duct 22 may include a first portion 80 and a second portion 82 coupled together to form the interior 36 of the duct 22. Alternatively, the duct 22 may be a single integrated or molded component. The duct 22 defines the receiving extension 24 proximate to the outlet 70. The receiving extension 24 is an integrally defined component, molded with the duct 22.

The receiving extension 24 defines the receiving cavity 26 therein, which is in fluid communication with the interior 36 of the duct 22. The receiving cavity 26 is offset or setback from a remainder of an inner surface 84 of the duct 22. In this way, the receiving cavity 26 forms an extension of the interior 36 of the duct 22. The receiving extension 24 generally defines a T-shaped cross-sectional shape to receive and engage the holder assembly 32.

The holder assembly 32 is configured to be selectively inserted into and removed from the receiving cavity 26. When disposed in the receiving cavity 26, the holder assembly 32 is incorporated into the duct assembly 20 to allow the diffusion of the scent. Additionally, when disposed in the receiving cavity 26, the holder assembly 32 does not substantially impinge on an airflow path through the interior 36 of the duct 22. The holder assembly 32 includes a body 90 with an inner wall 92, with the inner wall 92 spaced from the locating tracks 28, 30 and disposed toward the interior 36 of the duct 22. The inner wall 92 generally aligns with the inner surface 84 of the duct 22 adjacent to the receiving extension 24.

Figures 5, 6:
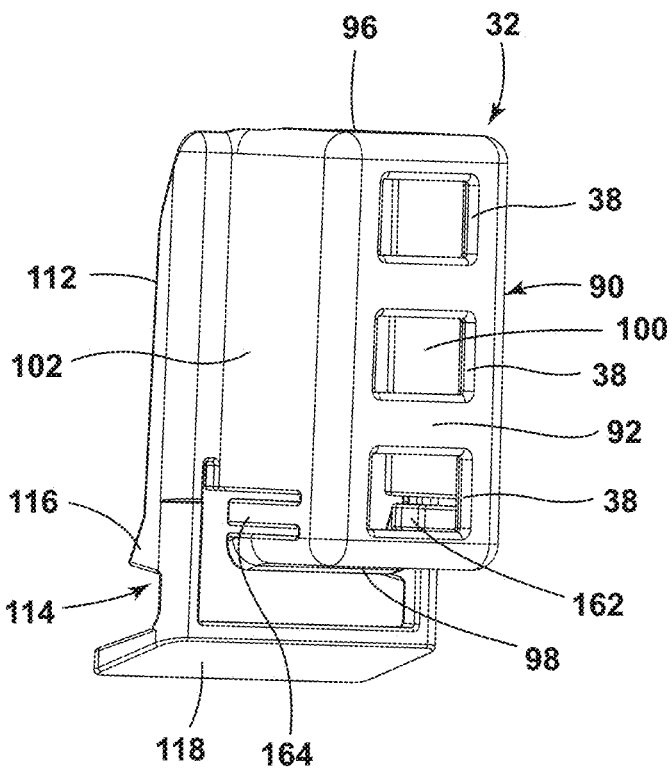
FIG. 5 is a side perspective view of a body of a holder assembly, according to the present disclosure.
FIG. 6 is a side perspective view of a body of a holder assembly, according to the present disclosure.

Referring to FIGS. 5 and 6, the body 90 of the holder assembly 32 forms a generally rectangular shape with an open side 94, the inner wall 92, two opposing end walls 96, 98, and two opposing sidewalls 100, 102. The inner wall 92 defines the openings 38 for providing fluid communication between the interior 34 of the holder assembly 32 and the interior 36 of the duct 22 (FIG. 4). In the illustrated configuration, the openings 38 are substantially similar shapes and sizes arranged in a linear configuration. However, additional or alternative configurations of the openings 38 are contemplated without departing the teachings herein.

The body 90 of the holder assembly 32 also includes slides 110, 112, which extend outwardly relative to the sidewalls 100, 102 and away from one another. In certain aspects, the slides 110, 112 are extensions of the sidewalls 100, 102. The slides 110, 112 extend substantially perpendicular to the sidewalls 100, 102 and then curve proximate a distal end of the slides 110, 112. At the distal ends, the slides 110, 112 extend parallel to the sidewalls 100, 102 forming a loose "S" configuration of the slides 110, 112.

The holder assembly 32 also includes a connector 114 coupled to the body 90. The connector 114 includes coupling features 116, which are illustrated as snap features coupled to each of the slides 110, 112 proximate to the second end wall 98. The coupling features 116 are substantially wedge-shaped to engage the duct 22 and retain the position of the holder assembly 32 relative to the duct 22. The connector 114 also includes a lever 118 that extends between and is coupled to the two coupling features 116. The connector 114 is constructed of a material that is configured to elastically deform. In this way, a user may apply force to the lever 118 in the direction of arrow 120, which is configured to move the lever 118 in the direction of the arrow 120 and, consequently, move the coupling features 116.

Referring still to FIGS. 5 and 6, the first end wall 96 defines grooves 128 extending from an end of the first end wall 96 toward the inner wall 92. The grooves 128 are spaced apart by projections 130. The grooves 128 are configured to receive locating features 132 of the duct 22 as described herein. Accordingly, the first end wall 96 having the grooves 128 and projections 130 assists with properly installing the holder assembly 32 in the duct 22.

Referring again to FIGS. 3 and 4, and still to FIGS. 5 and 6, the holder assembly 32 is configured to be inserted into the receiving cavity 26 with the first end wall 96 further into the duct 22 and the second end wall 98 proximate the outlet 70. Accordingly, the connector 114 is disposed adjacent to the outlet 70. As illustrated in FIG. 3, the receiving extension 24 includes a connecting wall 140 that extends between and partially defined the locating tracks 28, 30. The connecting wall 140 defines apertures 142 and the coupling features 116 are configured to be selectively disposed within the apertures 142 to couple the holder assembly 32 to the duct 22. As the holder assembly 32 is inserted into the receiving cavity 26, the connector 114 is configured to elastically deform as the coupling features 116 engage the surface 84 of the connecting wall 140 of the duct 22 and then snap engage into the apertures 142.

When coupling features 116 are disposed within the apertures 142, the lever 118 is configured to extend along the inner surface 84 of the duct 22 proximate to the outlet 70. In various examples, the lever 118 is configured to extend along the inner surface 84 adjacent to the receiving cavity 26 and the outlet 70. In this way, the user, such as a service technician, is configured to be able to engage the lever 118 from the floor space 66 of the front passenger seat 64 (FIG. 2). Upon applying force to the lever 118, the lever 118 is configured to adjust the coupling features 116 to disengage the coupling features 116 from the apertures 142 to allow removal of the holder assembly 32. In other words, the lever 114 is configured to adjust the coupling features 116 relative to the apertures 142 in response to a predefined force.

Figures 7, 8:
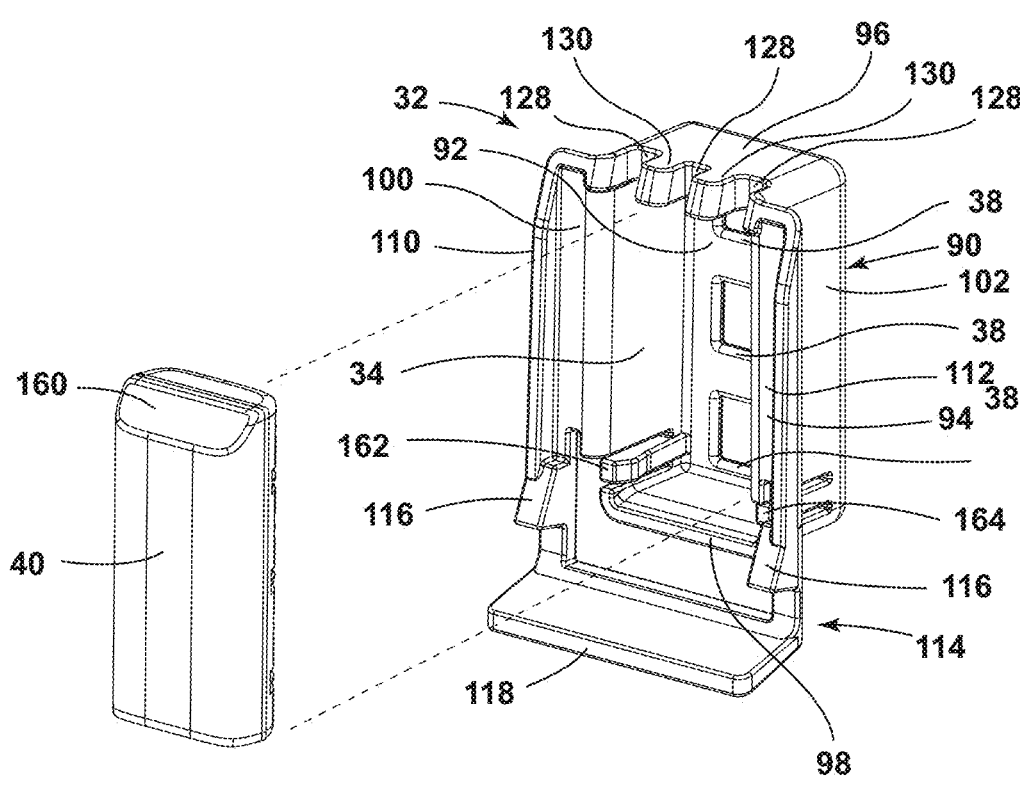
FIG. 7 is an exploded side perspective view of a holder assembly with a scented pad, according to the present disclosure.
FIG. 8 is a cross-sectional view of the body of the holder assembly of FIG. 6, taken along lines VIII-VIII, according to the present disclosure.
Figure 9:
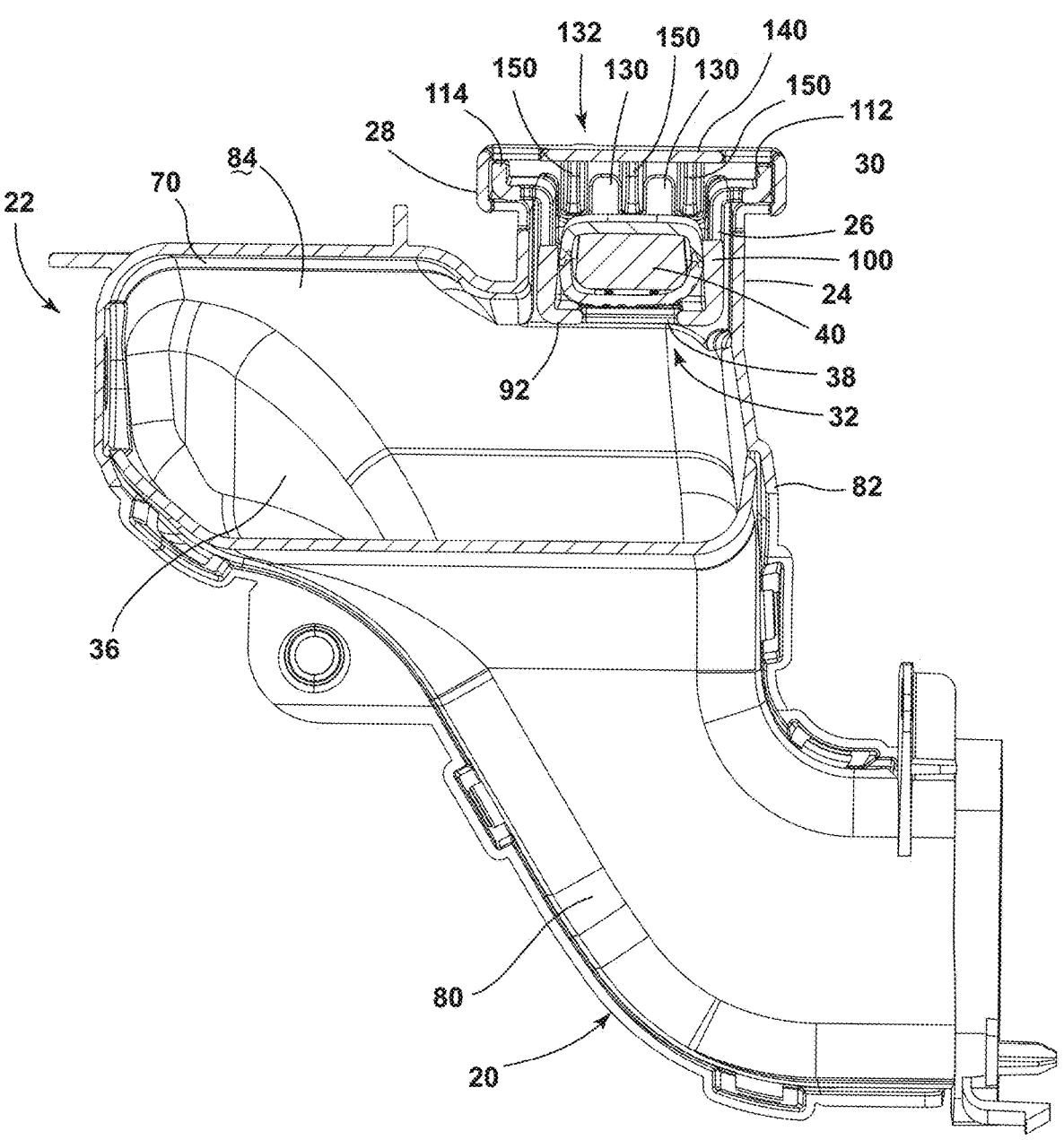
FIG. 9 is a cross-sectional view of a duct assembly with a holder assembly within a receiving cavity of a duct, according to the present disclosure.

Referring still to FIGS. 5 and 6, as well as FIGS. 7-9, the receiving extension 24 defines the locating tracks 28, 30 on opposing sides of the receiving extension 24, forming the overall "T" shape of the receiving extension 24. The slides 110, 112 of the holder assembly 32 are configured to be slidably received in the locating tracks 28, 30. The curve or "S" shape of the slides 110, 112 allows movement along an insertion/removal path, illustrated by arrow 148. The shape of the slides 110, 112 also minimizes other movement of the holder assembly 32, such as twisting, movement along a path normal to the insertion/removal path, etc., relative to the locating tracks 28, 30, where these other movements can cause rattling sounds.

The connecting wall 140 defines the locating features 132 configured as ribs 150 extending along the inner surface 84 thereof. The ribs 150 extend toward the interior 36 of the duct 22. The ribs 150 have a rounded or beveled engagement end 152, which is the end 152 closer to the outlet 70 of the duct 22. The rounded engagement end 152 may assist with engaging the first end wall 96 of the holder assembly 32 to properly align the holder assembly 32 for insertion. The ribs 150 are configured to be slidably received within the grooves 128 defined by the first end wall 96. In this way, the engagement between the ribs 150, the grooves 128, and the projections 130 maintains alignment of the holder assembly 32 within the receiving cavity 26 and provides feedback for proper insertion within the receiving cavity 26. This engagement also minimizes movement of the holder assembly 32 when fully inserted into the receiving cavity 26.

Referring again to FIGS. 3-9, the first end wall 96 is inserted into the receiving cavity 26 with the slides 110, 112 extending into the locating tracks 28, 30. The holder assembly 32 is slidably received with the ribs 150 sliding through the grooves 128 of the holder assembly 32. The holder assembly 32 is configured to continue to be inserted until the coupling features 116 are fully disposed within the apertures 142 defined by the receiving extension 24. To remove the holder assembly 32, the user applies a force to the lever 118 to move the coupling features 116 out of the apertures 142, and the holder assembly 32 is slidably removed along the locating tracks 28, 30 from the receiving extension 24.

Referring again to FIGS. 7 and 8, the holder assembly 32 is configured to hold the scented pad 40, which is utilized by the scent diffusing system 10 to diffuse the scent into the passenger compartment 14 (FIG. 2). The scented pad 40 may have a variety of configurations with different materials used for holding a scent and allowing the scent to diffuse through passing airflow. In the illustrated example, the scent is contained within an elongate pad 40, which has a substantially rectangular shape similar to the body 90 of the holder assembly 32.

The holder assembly 32 includes an interior locating feature 158. The interior locating feature 158 is configured as a ramp or wedge that extends from the first end wall 96 into the interior 34 of the holder assembly 32. Generally, the interior locating feature 158 is integrally defined with the first end wall 96. The interior locating feature 158 is defined proximate to ends of the grooves 128. Accordingly, the projections 130 also have an increased thickness to assist in locating and retaining the scented pad 40. In various examples, the interior locating feature 158 extends across the entire width of the body 90 between the two sidewalls 100, 102.

The scented pad 40 includes a chamfered edge 160, which is configured to engage the interior locating feature 158. The chamfered edge 160 of the scented pad 40 is configured to engage the interior locating feature 158, and this engagement assists with positioning the scented pad 40 within the interior 34 of the holder assembly 32. Further, this engagement also assists in retaining the scented pad 40 in position within the body 90 to minimize any rattling sounds.

Additionally, the holder assembly 32 includes retaining features 162, 164 defined by the sidewalls 100, 102. The retaining features 162, 164 are each configured as a projection 130 between opposing notches, allowing the retaining features 162, 164 to elastically deform independently of the sidewalls 100, 102. The retaining features 162, 164 have a biasing force toward one another, generally from the construction of the body 90 and the materials forming the body 90. As the scented pad 40 is inserted into the interior 34 of the holder assembly 32, the scented pad 40 elastically deforms the retaining features 162, 164 against the biasing force. While the scented pad 40 is fully inserted into the interior 34 of the holder assembly 32 for the biasing force of the retaining features 162, 164 maintains engagement with the scented pad 40 to retain the scented pad 40 in the position within the interior 34 of the holder assembly 32. The interior locating feature 158 and the retaining features 162, 164 are configured to hold the scented pad 40 in position, which is advantageous for preventing rattling noise and movement of the scented pad 40 within the body 90, which may be caused by the airflow through the duct assembly 20.

Figure 10:
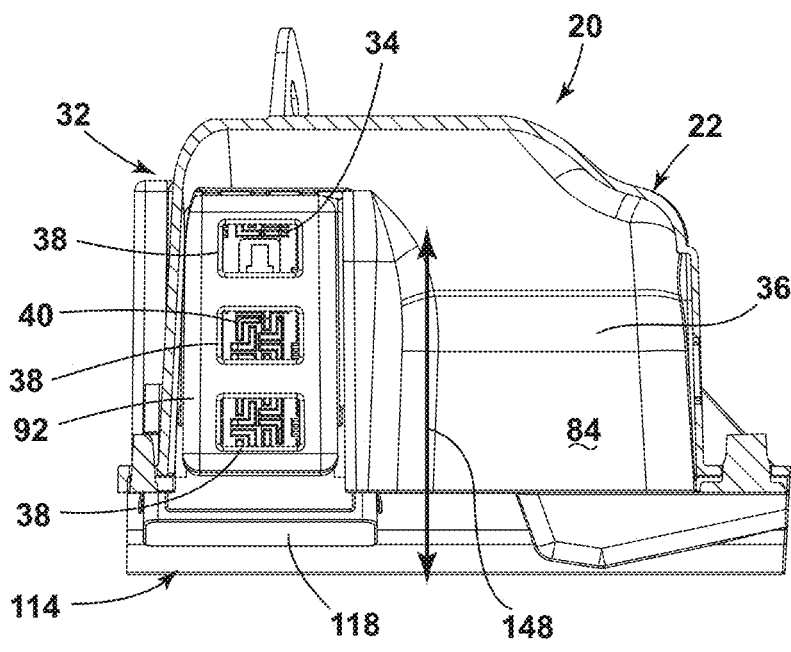
FIG. 10 is a cross-sectional view of a duct assembly with a holder assembly within a receiving cavity of a duct, according to the present disclosure.
Figure 11:
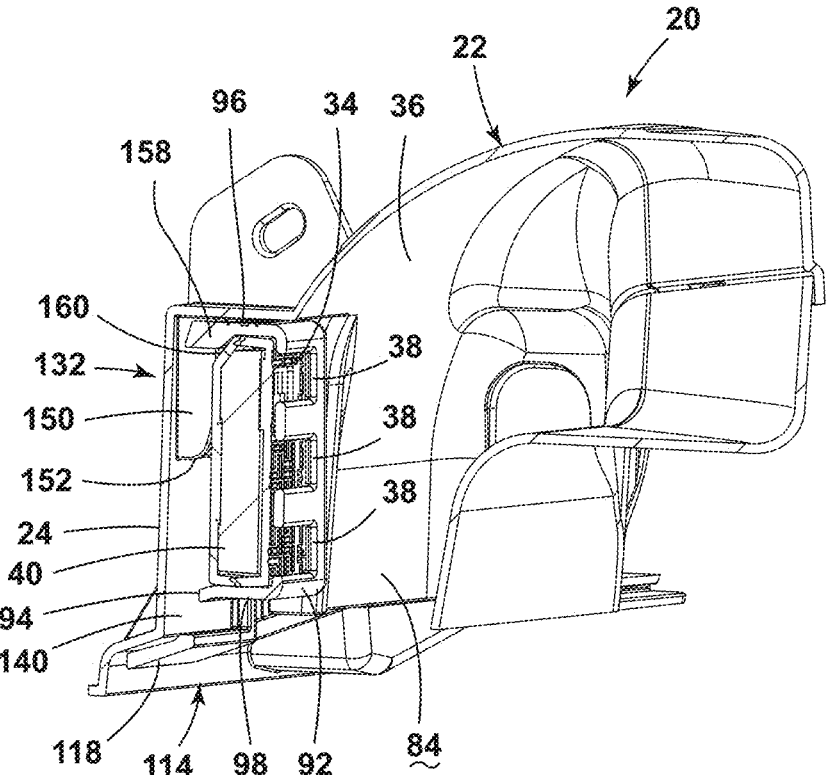
FIG. 11 is a cross-sectional view of a duct assembly with a holder assembly within a receiving cavity of a duct, according to the present disclosure.

Referring to FIGS. 10 and 11, the holder assembly 32 is disposed within the receiving cavity 26 with the first end wall 96 disposed adjacent to or abutting on the surface 84 of the receiving extension 24 and the lever 118 extending out of the receiving cavity 26 along the inner surface 84 of the duct 22 proximate the outlet 70. The inner wall 92 of the holder assembly 32 defining the openings 38 is disposed proximate to, and generally aligned with, the inner surface 84 of the duct 22 adjacent to the receiving extension 24. The interior 34 of the holder assembly 32 is in fluid communication with the interior 36 of the duct 22 via the openings 38. In this way, as air flows through the interior 36 of the duct 22 the air also flows through the openings 38, into and out of the interior 34 of the holder assembly 32. Accordingly, as air flows through the duct assembly 20, including through the holder assembly 32, the scent from the scented pad 40 is diffused into the airflow and into the passenger compartment 14.

Figure 12:
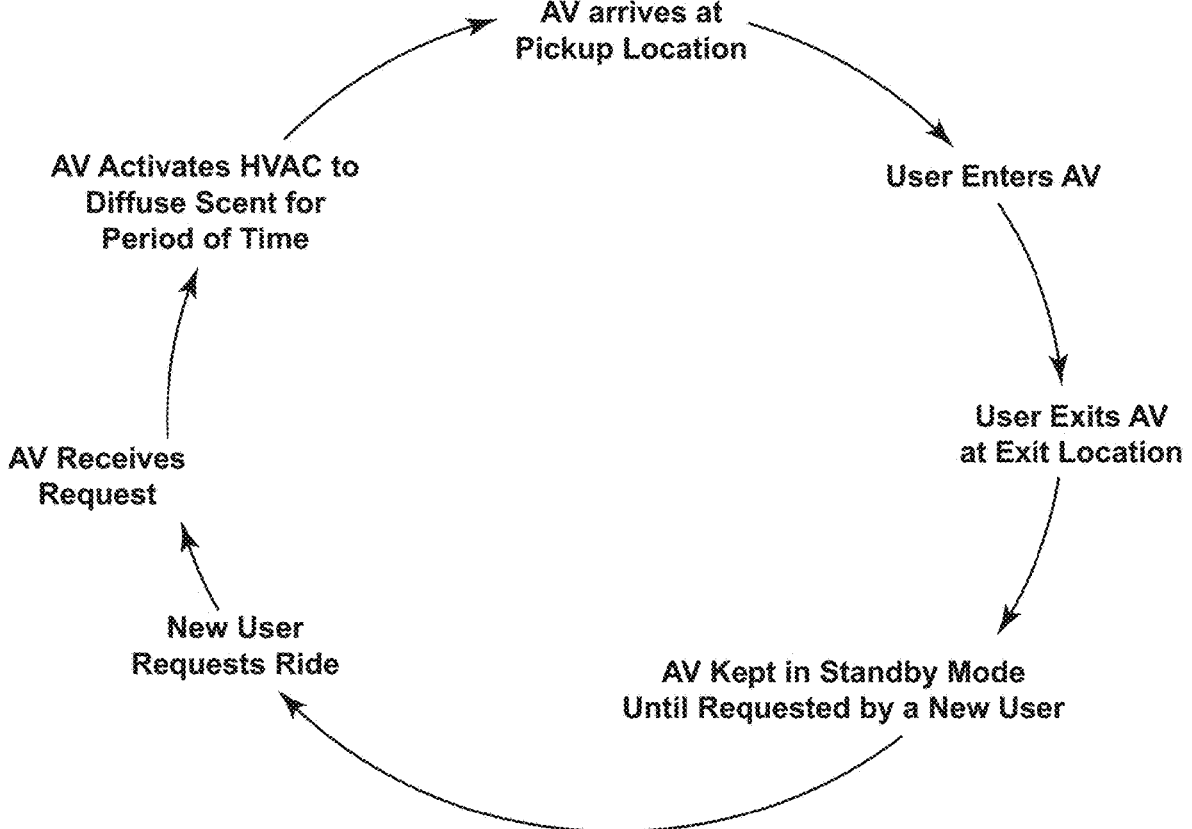
FIG. 12 is a flow chart of a method of using a vehicle with a scent diffusing system and ride services, according to the present disclosure.

Referring to FIG. 12, as well as FIGS. 1-11, the vehicle 12 may be utilized for ride-providing or ride-sharing services for multiple passengers throughout the day. The scent diffusing system 10 is configured to activate the HVAC system 16 to direct the airflow through the duct assembly 20 prior to each new passenger entering the vehicle 12. In certain aspects, the HVAC system 16 includes an interior door flap or valve, which directs the airflow through the duct assembly 20 in certain circumstances and bypasses the duct assembly 20 in other circumstances based on signals from the controller 18. In this way, the passenger may utilize the HVAC system 16 for heating or cooling but may not diffuse the scent into the passenger compartment 14 while doing so.

The HVAC system 16 may be operated in a scent diffusing mode with the scent diffusing system 10 to provide scented air to the passenger compartment 14 and a standard operating mode, which bypasses the duct assembly 20 with the holder assembly 32 to provide the conditioned air to the passenger compartment 14. The scent may be selectively diffused in a manner that is generally pleasant and not overwhelming to the passengers.

The controller 18 includes a processor, a memory, and other control circuitry. Instructions or routines are stored within the memory and executable by the processor. The controller 18 disclosed herein may include various types of control circuitry, digital or analog, and may include the processor, a microcontroller, an application specific circuit (ASIC), or other circuitry configured to perform the various input or output, control, analysis, or other functions described herein. The memory described herein may be implemented in a variety of volatile and nonvolatile memory formats. The routines include operating instructions to enable various functions described herein.

The controller 18 also includes communication circuitry configured for bidirectional wired and wireless communication. The controller 18 may be configured to communicate with a server (e.g., cloud servers, Internet-connected databases, computers, etc.) having an application or software related to ride-providing or ride-sharing services via a communication interface. The communication interface may correspond to a variety of communication protocols configured to distribute data among various electronic devices. For example, the controller 18 is configured to communicate with a remote server and/or a remote device, directly or indirectly, to allow the vehicle 12 to be used with ride-providing and ride-sharing services.

In operation, as illustrated in FIG. 12, a new user requests a ride generally via a software application on a remote device, such as a phone or tablet. The request is communicated to the server and then to the vehicle 12. The vehicle 12 receives the request, which includes a pickup location and drop off location. After receiving the request, the vehicle 12 travels to the pickup location. In autonomous vehicle 12 examples, the vehicle 12 may utilize the sensors 52 and computing devices to travel to the pickup location. In the semi-autonomous or non-autonomous vehicles 12, the controller 18 may further communicate the request to the operator, via a separate device, such as a phone, or an interior display to direct the vehicle 12 to the pickup location.

On the way to the pickup location, the vehicle 12 is configured to activate the HVAC system 16 in the scent diffusing mode to diffuse the scent. The scent may be diffused into the passenger compartment 14 for a predefined period of time and/or to a predefined level, as sensed by an interior sensor. The scent is diffused into the passenger compartment 14 from the foot space 66 of the front passenger seat, but not continually diffused. The controller 18 may be configured to utilize a global positioning system (GPS) and/or real-time traffic updates to determine an amount of time or distance to the pickup location. The controller 18 is configured to activate the HVAC system 16 in the scent diffusing mode, directing the airflow through the duct assembly 20 at a predefined time or distance from the pickup location. In this way, the scent may be diffused into the passenger compartment 14 between receiving the ride request and arriving at the pickup location. After the scent has been diffused for the predefined period of time or to the predefined level, the controller 18 is configured to deactivate the scent diffusing mode to stop the additional diffusing of the scent into the passenger compartment 14. The controller 18 may deactivate the HVAC system 16 or adjust the HVAC system 16 to the standard operating mode.

The vehicle 12 then arrives at the pickup location and the passenger enters the vehicle 12. The vehicle 12 transports the user to the drop off location. During the time the passenger is within the vehicle 12, the HVAC system 16 may be operated in the standard operating mode. Once the passenger exits the vehicle 12, the vehicle 12 is kept in a standby mode until a new user request is received or the human operator may use the vehicle 12 separately from the ride-providing or ride-sharing services.

Referring to FIGS. 1-12, the scent diffusing system 10 is utilized to diffuse the scent into the passenger compartment 14 prior to new passengers entering the vehicle 12 to provide a pleasant aroma within the vehicle 12. The controller 18 is configured to control or adjust the HVAC system 16 between the scent diffusing mode, directing air through the duct assembly 20 with the holder assembly 32 to diffuse the scent, and the standard operating mode, directing air to the passenger compartment 14 via different ducting and bypassing the duct assembly 20 with the holder assembly 32. The position of the holder assembly 32 by the outlet 70 allows the holder assembly 32 to be generally concealed from view of the passengers within the vehicle 12 while providing efficient and convenient access by a service technician. The technician can reach the lever 118 to apply the force to remove the holder assembly 32 to change the scented pad 40.

Use of the present device may provide for a variety of advantages. For example, the duct assembly 20 may be utilized to diffuse the scent via the airflow traveling through the duct assembly 20 into the passenger compartment 14. Additionally, the scent diffusing system 10 may control the HVAC system 16 to direct airflow through the duct assembly 20 at certain times and bypass the duct assembly 20 at others. Additionally, the holder assembly 32 is configured to slidably engage the duct assembly 20 for efficient insertion and removal of the holder assembly 32, which may be advantageous for servicing the holder assembly 32. Further, the holder assembly 32 is configured to be fully in the receiving cavity 26 to be accessible for a technician and concealed from view of passengers. Also, the duct 22 and the holder assembly 32 each have locating features 132 for maintaining the position of the various components and reducing noise. Additional benefits or advantages may be realized and/or achieved.

According to various examples, a scent diffusing system for a vehicle includes a passenger compartment. A heating, ventilation, and air conditioning system is in fluid communication with the passenger compartment. A controller is in communication with the heating, ventilation, and air conditioning system. A duct assembly extends between the heating, ventilation, and air conditioning system and the passenger compartment. The duct assembly includes a duct including a receiving extension defining a receiving cavity. The receiving extension defines locating tracks. A holder assembly is slidably received within the locating tracks. An interior of the holder assembly is in fluid communication with an interior of the duct via openings defined by the holder assembly. A scented pad is disposed within the interior of the holder assembly. The controller is configured to activate the heating, ventilation, and air conditioning system to direct air through the duct, through the interior of the holder assembly, and into the passenger compartment to diffuse a scent within the passenger compartment. Embodiments of the present disclosure may include one or a combination of the following features:

the controller is configured to communicate with a remote device to receive a ride request with a pickup location;

the controller is configured to activate the heating, ventilation, and air conditioning system to direct the air through the duct for a predefined period of time between receiving the ride request and arriving at the pickup location;

the duct defines apertures;

the holder assembly includes snap features configured to be selectively disposed within the apertures to couple the holder assembly to the duct;

an outlet of the duct is disposed proximate to a foot space of a passenger seating area within the passenger compartment;

the holder assembly has an inner wall that defines the openings;

the inner wall aligns with an inner surface of the duct adjacent to the receiving extension; and the holder assembly defines outwardly extending slides configured to be received by the locating tracks.

According to various examples, a vehicle duct assembly for a heating, ventilation, and air conditioning system includes a duct including a receiving extension defining a receiving cavity. The receiving extension defines locating tracks. A holder assembly is selectively disposed within the receiving cavity. The holder assembly includes slides configured to be slidably received within the locating tracks. An interior of the holder assembly is in fluid communication with an interior of the duct via openings defined by the holder assembly. A scented pad is disposed within the interior of the holder assembly. Air directed through the duct by said heating, ventilation, and air conditioning system flows through the interior of the holder assembly to diffuse a scent within the air. Embodiments of the present disclosure may include one or a combination of the following features:

the holder assembly includes an interior locating feature extending from an end wall into the interior of the holder assembly;

the scented pad defines a chamfered edge configured to engage the interior locating feature;

the holder assembly includes coupling features configured to selectively engage the receiving extension to couple the holder assembly to the duct;

the receiving extension defines apertures and the coupling features are selectively disposed within the apertures;

the holder assembly includes a lever coupled to the coupling features;

movement of the lever is configured to move the coupling features relative to the apertures to disengage the holder assembly from the duct;

the openings are aligned with an inner surface of the duct adjacent to the receiving extension; and the holder assembly is coupled to the duct proximate to a duct outlet.

According to various examples, a duct assembly for a vehicle includes a duct with a receiving extension defining a receiving cavity. The receiving extension defines apertures in a connecting wall thereof. A holder assembly is configured to receive a scented pad. The holder assembly includes a body that defines an opening. An interior of the body is in fluid communication with an interior of the duct via the openings. Snap features are coupled to the body, wherein the snap features are selectively disposed within the apertures to couple the holder assembly to the receiving extension. A lever is coupled to the snap features. The lever is configured to disengage the snap features from the apertures in response to a predefined force. Embodiments of the present disclosure may include one or a combination of the following features:

the receiving extension defines locating tracks;

the body of the holder assembly includes slides configured to be slidably receiving within the locating tracks;

the connecting wall defines ribs extending toward an interior of the duct;

the body of the holder assembly defines grooves to receive the ribs of the connecting wall;

the body of the holder assembly includes an interior locating feature for engaging the scented pad;

the lever is disposed proximate to a duct outlet when the holder assembly is disposed within the receiving cavity; and the lever extends along an inner surface of the duct adjacent to the receiving cavity and the duct outlet.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the invention as shown in the exemplary examples is illustrative only. Although only a few examples of the present innovations have been described in detail in this disclosure, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connectors or other elements of the system may be varied, the nature or number of adjustment positions provided between the elements may be varied. It should be noted that the elements and/or assemblies of the system might be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary examples without departing from the spirit of the present innovations.

Modifications of the disclosure will occur to those skilled in the art and to those who make or use the disclosure. Therefore, it is understood that the embodiments shown in the drawings and described above are merely for illustrative purposes and not intended to limit the scope of the disclosure, which is defined by the following claims, as interpreted according to the principles of patent law, including the doctrine of equivalents.

It is to be understood that variations and modifications can be made on the aforementioned structure without departing from the concepts of the present disclosure, and further it is to be understood that such concepts are intended to be covered by the following claims unless these claims by their language expressly state otherwise.

What is claimed is:

1. A scent diffusing system for a vehicle, comprising:

a passenger compartment;

a heating, ventilation, and air conditioning system in fluid communication with the passenger compartment;

a controller in communication with the heating, ventilation, and air conditioning system; and a duct assembly extending between the heating, ventilation, and air conditioning system and the passenger compartment, wherein the duct assembly includes:

a duct including a receiving extension defining a receiving cavity, and wherein the receiving extension defines locating tracks, wherein the duct defines apertures;

a holder assembly slidably received within the locating tracks, wherein an interior of the holder assembly is in fluid communication with an interior of the duct via openings defined by the holder assembly, and wherein the holder assembly includes snap features configured to be selectively disposed within the apertures to couple the holder assembly to the duct, and further wherein a lever is configured to disengage the snap features from the apertures; and a scented pad disposed within the interior of the holder assembly, and wherein the controller is configured to activate the heating, ventilation, and air conditioning system to direct air through the duct, through the interior of the holder assembly, and into the passenger compartment to diffuse a scent within the passenger compartment.

2. The scent diffusing system of claim 1, wherein the controller is configured to communicate with a remote device to receive a ride request with a pickup location.

3. The scent diffusing system of claim 2, wherein the controller is configured to activate the heating, ventilation, and air conditioning system to direct the air through the duct for a predefined period of time between receiving the ride request and arriving at the pickup location.

4. The scent diffusing system of claim 1, wherein an outlet of the duct is disposed proximate to a foot space of a passenger seating area within the passenger compartment.

5. The scent diffusing system of claim 1, wherein the holder assembly has an inner wall that defines the openings, and wherein the inner wall aligns with an inner surface of the duct adjacent to the receiving extension.

6. The scent diffusing system of claim 1, wherein the holder assembly defines outwardly extending slides configured to be received by the locating tracks.

7. A vehicle duct assembly for a heating, ventilation, and air conditioning system, comprising:

a duct including a receiving extension defining a receiving cavity, and wherein the receiving extension defines locating tracks;

a holder assembly selectively disposed within the receiving cavity, wherein the holder assembly includes slides configured to be slidably received within the locating tracks, and wherein an interior of the holder assembly is in fluid communication with an interior of the duct via openings defined by the holder assembly, wherein the holder assembly includes coupling features configured to selectively engage the receiving extension to couple the holder assembly to the duct, and wherein the holder assembly includes a lever coupled to the coupling features, and further wherein the lever is configured to disengage the holder assembly from the duct via movement of the lever; and a scented pad disposed within the interior of the holder assembly, and wherein air directed through the duct by said heating, ventilation, and air conditioning system flows through the interior of the holder assembly to diffuse a scent within the air.

8. The vehicle duct assembly of claim 7, wherein the holder assembly includes an interior locating feature extending from an end wall into the interior of the holder assembly, and wherein the scented pad defines a chamfered edge configured to engage the interior locating feature.

9. The vehicle duct assembly of claim 7, wherein the receiving extension defines apertures and the coupling features are selectively disposed within the apertures.

10. The vehicle duct assembly of claim 9, wherein movement of the lever is configured to move the coupling features relative to the apertures.

11. The vehicle duct assembly of claim 7, wherein the openings are aligned with an inner surface of the duct adjacent to the receiving extension.

12. The vehicle duct assembly of claim 7, wherein the holder assembly is coupled to the duct proximate to a duct outlet.

13. A duct assembly for a vehicle comprising:

a duct including a receiving extension defining a receiving cavity, wherein the receiving extension defines apertures in a connecting wall thereof; and a holder assembly configured to receive a scented pad, wherein the holder assembly includes:

a body defining an opening, wherein an interior of the body is in fluid communication with an interior of the duct via openings;

snap features coupled to the body, wherein the snap features are selectively disposed within the apertures to couple the holder assembly to the receiving extension; and a lever coupled to the snap features, wherein the lever is configured to disengage the snap features from the apertures in response to a predefined force.

14. The duct assembly of claim 13, wherein the receiving extension defines locating tracks, and wherein the body of the holder assembly includes slides configured to be slidably received within the locating tracks.

15. The duct assembly of claim 13, wherein the connecting wall defines ribs extending toward an interior of the duct, and wherein the body of the holder assembly defines grooves to receive the ribs of the connecting wall.

16. The duct assembly of claim 13, wherein the body of the holder assembly includes an interior locating feature for engaging the scented pad.

17. The duct assembly of claim 13, wherein the lever is disposed proximate to a duct outlet when the holder assembly is disposed within the receiving cavity.

18. The duct assembly of claim 17, wherein the lever extends along an inner surface of the duct adjacent to the receiving cavity and the duct outlet.

19. The scent diffusing system of claim 1, wherein a movement of the lever is configured to allow removal of the holder assembly from the duct.

20. The vehicle duct assembly of claim 7, wherein the holder assembly is configured to be removed from the duct slidably along the locating tracks.

*   *   *   *   *